US00PP08541P

United States Patent [19]

Streeter

[11] Patent Number: Plant 8,541

[45] Date of Patent: Jan. 11, 1994

[54] *CATTLEYA LODDIGESII* VAR. HARRISONIANA STREETER'S CHOICE FCC/AOS

[76] Inventor: Robert J. Streeter, 2908 Via Rivera, Palos Verdes Estates, Calif. 90274

[21] Appl. No.: 448

[22] Filed: Jan. 4, 1993

[51] Int. Cl.[5] ..... A01H 5/00
[52] U.S. Cl. ..... Plt./87.3
[58] Field of Search ..... Plt. 87.3

*Primary Examiner*—James R. Feyrer

[57] ABSTRACT

The subject of this application is a new and distinct variety of orchid, resulting from a mutation of a plant in a tissue cultured population of *C. loddigesii* var. Harrisoniana. The cultivar of the application is outstanding because of its superior flower quality to all of the same market and botanical class which combines heavy texture with its glowing sheen of rose-lavender petals and white-cream labellum tipped with lavender. The shape of the flower is superior to all equivalent cultivars of this species. Because of its exceptional substance the flowers have a longer bloom life than all other cultivars of the species.

1 Drawing Sheet

DISCOVERY OF THE NEW VARIETY

I. The orchid was discovered in a cultivated area by the applicant in 1984 from a group of tissue cultured plants of species *Cattleya loddigesii* var. Harrisoniana. The cultivar showed outstanding characteristics in substance, which I refer to the thickness of the pedals being twice the normal, measuring 1.01 mm–1.23 mm versus 0.59–0.66 mm of the parent. The size being larger, approximately one centimeter in over all width greater than parent variety, measuring 10 cm. versus 9 cm of the parent. The width of the pedal and dorsal, lateral sepals are approximately 20% greater than the parent variety. Dorsal sepal 2.7 cm. wide, 5.2 cm long; petal 4.1 cm. wide, 5.4 cm. long; lateral sepals 2.6 cm. wide, 5.0 cm. long; lip 3.8 cm. wide, 5.2 cm. long. (These measurements taken from the Award Quarterly of The American Orchid Society) which could indicate its likelihood of being a polyploid. The remaining plants of this cloning exhibited only typical species characteristics.

With the later observations of superior flower quality and growth habits, the cultivar name "Streeter's Choice" was given to this particular plant to identify its from all others carrying this species name and the remaining plants of the tissue cultured population.

ASEXUAL REPRODUCTION

After "Streeter's Choice" was recognized as an outstanding cultivar the plant was placed in a laboratory for tissue propagation in April 1987. The laboratory being operated by The H. and R. Nurseries, 41–240 Hihimanu, Waimanalo, Hawaii 06795. During the following years, a number of plants have been asexually produced by the meristem tissue culture method from it. These are all being asexually reproduced from the original cultivar.

The propagations have reproduced true to the original plant in both plant and flower characteristics, being exactly the same as the original mutation.

BRIEF DESCRIPTION OF THE DRAWING

The first photograph shows the flower. The second photograph shows plant growth habit and carriage of flower.

Color specifications presented in the following detailed botanical description as taken from The R.H.S. Colour Charts, The Royal Horticultural Society, London, 1986, in association with the Flower Council of Holland, Leiden, except where ordinary descriptions of color have sufficiently clear meaning.

DESCRIPTION OF PLANT

The plant growth habit of this cultivar is typical of bifoliate (two leaved) cattleyas with the exception of its heavy leaf substance. The thickness measures 4 mm versus 2 mm of the parent. The psuedobulb at maturity are 32–34 centimeters in height with a diameter of 1.5 cm versus 20–23 cm of the parent with a diameter of 1.2 cm. The leaf length range 15–17 cm long with a width of 6 cm versus, 10–11 cm long and 5 cm wide of the parent. A fully matured plant can attain the height of 36–38 centimeters. The rhizome is sturdy and compact, leading into new growth, becoming a naturally erect pseudobulb. At maturity leaves are produced and a sheath is formed in the axils of the leaves, through the sheath of a flower stalk is produced and an inflorescence bearing a spray of 4 to 6 flowers from an extra strong stem being carried well above the foliage. This cultivar will normally flower only once a year in late spring or summer.

The cultivar "Streeter's Choice" is possibly a tetraploid with 80 chromosomes as apposed to the normal 40. A chromosome count has not been made to the time of this application. It is being use to hybridize, both as a pod parent and a pollen parent. It produces a large seed pod approx. 10 cm. long and 5 cm giving viable seed generously. (Thousands) The progeny have not flowered at this time. The cultivar "Streeter's Choice" has been tested and found to be virus free and pathogen free, as well as the plant of the meristem population.

DESCRIPTION OF THE FLOWER

The inflorescence of this plant are borne on long pedicels which are thick and stout and have a green color which about matches that of the foliage. Flowers are presented at an angle of about 90 degrees to the axis of the pedicels on deep green peduncles of sufficient strength and girth to retain flower position without supplemental support for the life of the flower.

Orchids of this plant might be regarded as representative of approaching the best of those of the species; having outstanding coloration and color blending and contrast, and an appealing balance of sizes between sepals, petals, column and labellum. Sepals and petals are of identical color and hue, near RHS 72B. Sepals are ovate and have an entire margin. Coloration is substantially solid with veining being very inconspicuous. Top and bottom surfaces are the same in color expression which is substantially stable for the long life of the flowers. Petals are of slightly larger size than the sepals and are similar in general, but of slightly blunter overall shape. Petal margins characteristically contain randomly placed small, occasional indentations, and small shallow crinkles as opposed to the smooth margins of the sepals. While midribs and veining of the petals is detectable, they remain quite inconspicuous, giving the effect of a solid color of sepals and petals from a distance. Petals are imbricate over sepals for about half of the length of both structures. Flowers are slightly cupped, with the tips of both sepals and petals slightly reflexing to soften the shape of apexes and give an unusually attractive rounded effect to the whole flower.

The labellum (lip) of this orchid is approximately the same size as the petals in outward appearance, but somewhat wider in breadth when measured flat, across the two top lobes. The two top lobes assume an angle intermediate to the petals and the column in a fully open flower. The margin is distinctively finely crimped over the major extent. The under surface of the lip is of about the same color as sepals and petals, but only the marginal portion of the top surface of the lip approach this color and hue. The dark marginal color gradually blends or washes to a creamy white, approaching China White, with the central surface on either side of the midrib of the bottom lobe, expressing yellowish shading near green-yellow RHS 1D over the predominant white color of the lip. Veining is slightly more intensely colored around a characteristic dimple on the midrib between the central yellow spot and the margin of the bottom lobe. The column of this plant might most accurately be described as nose shaped; being rather large for the species. The column is slightly less than one half the length of the lip and forms a gently arched hood which is nearly framed by the top outward lobes of the lip on either side, and is uniformly white in color. The column nearly completely encloses the white ovary, only the apex of which can be viewed beneath the uneven, basal margin of the column. Lateral portions of the column flare broadly relative to the rounded bridge of the column and render the effect of substantially an isosceles triangle in plan for the column as a whole.

PLANT PART COLORATION

Sepal and petals are of a red-purple coloration which is substantially uniform, and near RHS 72B. Coloration is smooth and solid. The Column in the center of the flower is an off-white, near China White, as is the predominant and central portion of the lip. The central portion of the lip below the column is slightly but clearly shaded with a color approaching RHS green yellow group 1D. The lip center portion is shaded with RHS 3C. Lip margins are suffused with RHS 66D or darker toward the edge, and gradually changing to white toward the central portion of the lip. Margin coloration is darkest and heaviest in the marginal portions of the bottom lobe of the lip.

The roots are greenish with an over lay of a grayish or silver velamen, when wet becoming predominantly green. (Typical of most Cattleya roots.) Rhizomes and pseudobulbs are also the typical light cress-green depending on light exposure. The deepness of the green will increase with less light. The leaves are slightly darker green, with a lighter under side. The sheath and pedicel match the lighter green of the under side of the leaf.

I claim:

1. A new and distinct variety of *Cattleya loddigesii* orchid plant, substantially as described and illustrated, resulting as a somoclonal variation from tissue culture of 'Harrisoniana', which is particularly distinguished from its parent and other members of the market and botanical class by having superior heavy flower texture: and by having larger, flatter, and more rounded flower segments which render longer lasting flowers.

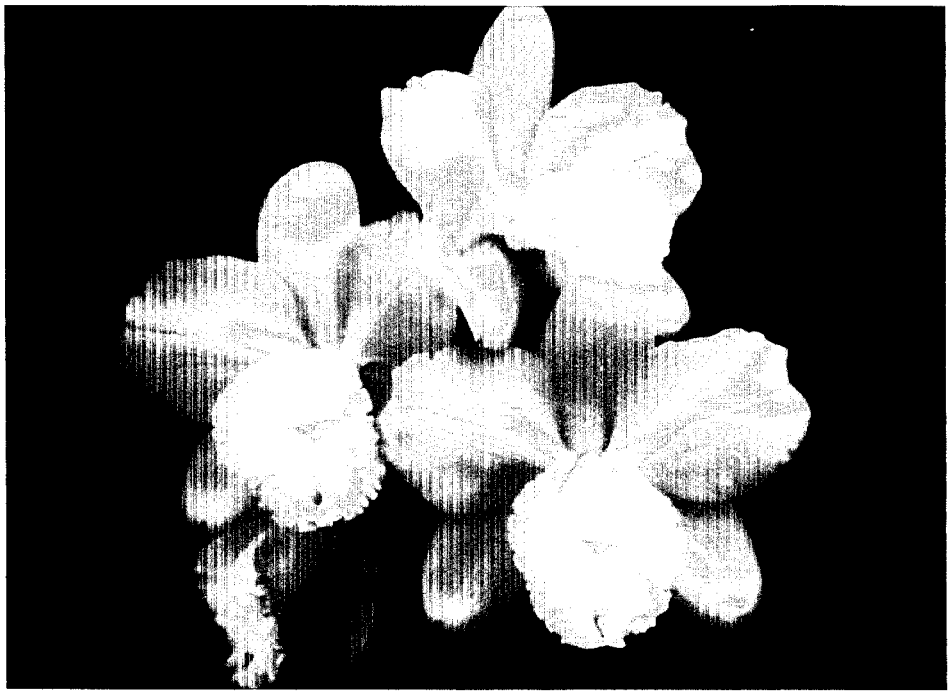
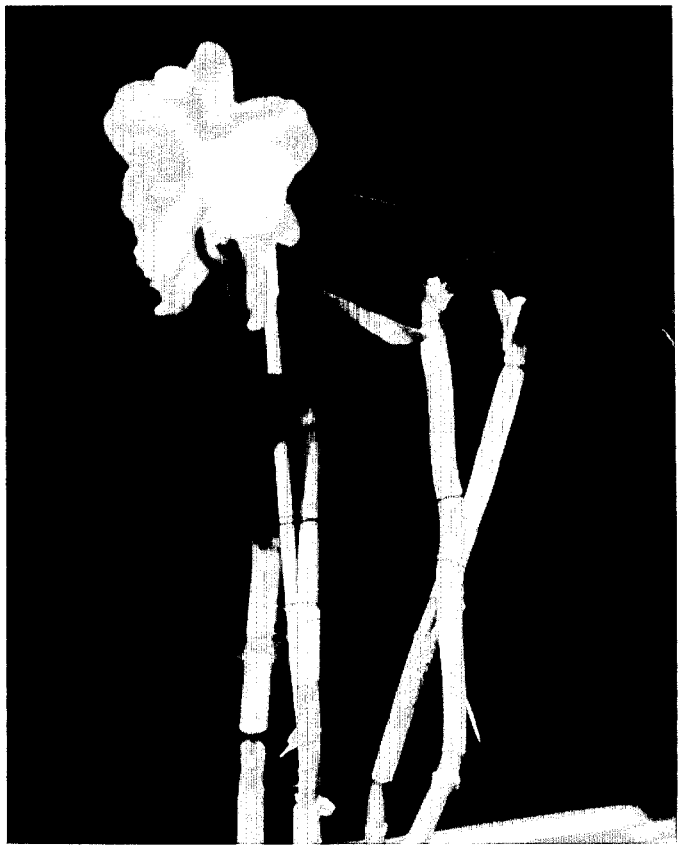

* * * * *